United States Patent [19]

Guido

[11] Patent Number: 5,342,397
[45] Date of Patent: Aug. 30, 1994

[54] CUTTING EDGE AND TAPERCUT NEEDLES HAVING A BLUNT TIP

[75] Inventor: Ronald Guido, Annandale, N.J.

[73] Assignee: Ethicon, Inc., Somerville, N.J.

[21] Appl. No.: 138,679

[22] Filed: Oct. 18, 1993

[51] Int. Cl.⁵ ............................................. A61B 17/00
[52] U.S. Cl. ................................. 606/222; 606/224
[58] Field of Search ............................. 606/222-227; 66/116, 117; D3/28

[56]  References Cited
U.S. PATENT DOCUMENTS

| | | | |
|---|---|---|---|
| 4,133,339 | 1/1979 | Naslund | 606/222 |
| 4,392,495 | 7/1983 | Bayers | 606/224 |
| 4,607,505 | 8/1986 | Dünker et al. | 66/117 |
| 4,966,143 | 10/1990 | Meinershagen | 606/103 |
| 5,123,910 | 6/1992 | McIntosh | 606/223 |

*Primary Examiner*—Stephen C. Pellegrino
*Assistant Examiner*—Gary Jackson
*Attorney, Agent, or Firm*—Emil Richard Skula

[57]  ABSTRACT

Blunt tip cutting edge needles which are suitable for use in suturing cutaneous tissues of the body while at the same time significantly reducing the probability of skin penetration of the gloved hand of an operator are disclosed. The needle includes a blunt tip and an integral cutting section having at least one cutting edge. The blunt tip blends smoothly with an outer surface of a distal end of the cutting portion such that the blunt tip has no sharp edges or discontinuities.

15 Claims, 2 Drawing Sheets

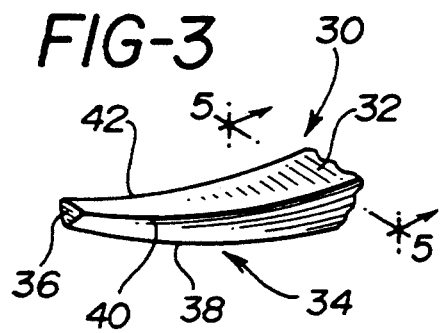
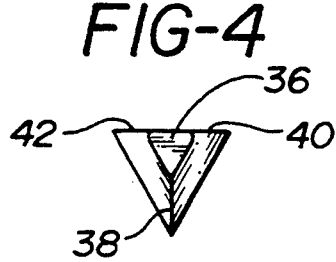
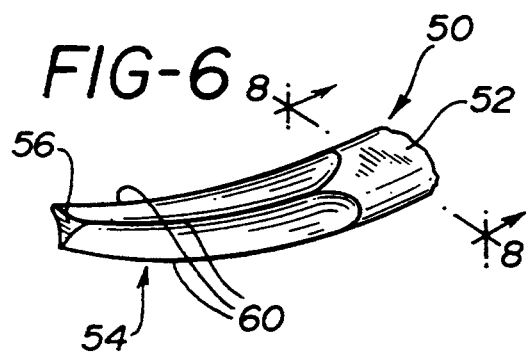
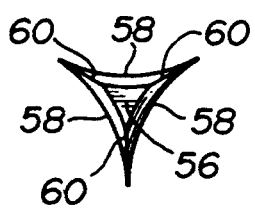
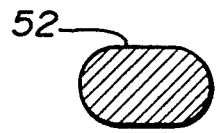
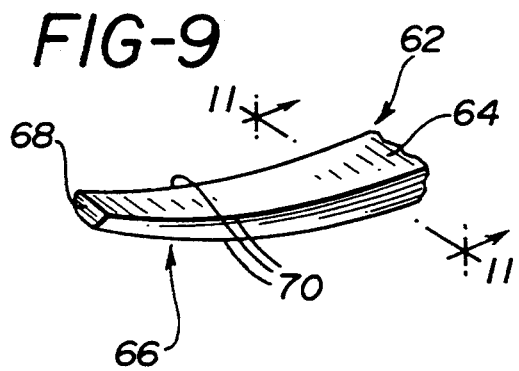
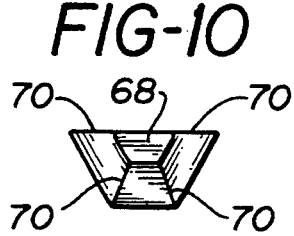
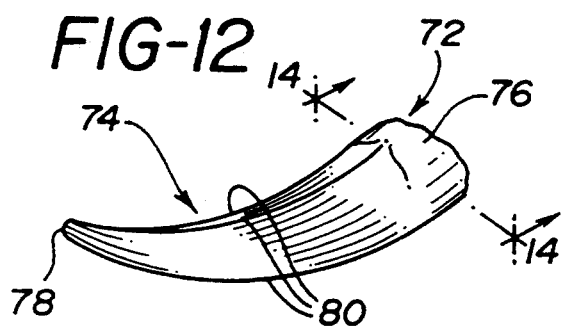
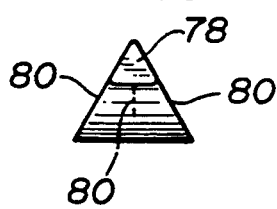

CUTTING EDGE AND TAPERCUT NEEDLES HAVING A BLUNT TIP

BACKGROUND OF THE INVENTION

1. Field of the Invention

This invention relates generally to surgical needles and, more particularly, to cutting edge and tapercut needles having a blunt tip for use in suturing cutaneous tissues of the body while at the same time decreasing potential skin penetration of the gloved hand of an operator.

2. Description of the Prior Art

In the design of surgical needles it is desirable for the needle to easily penetrate and smoothly pass through the tissue being sutured. The needle should be designed so as to minimize the resistance of the tissue to the passage of the entire needle through the tissue. The ease of penetration is dependent upon the sharpness of the needle point. Once the needle has penetrated the tissue, the body of the needle must be drawn through the opening in the tissue. This should be done with minimal force, and the needle should be shaped so that it will move smoothly through the opening. With cutting edge needles, widening of a hole made by initial penetration is effected by the cutting edge(s) as they slide through the tissue until there is a fully developed hole. Thus, in the design of surgical needles, it is desirable to make the cutting edge(s) and the point of the needle as sharp as possible.

Recently, another design criteria has surfaced as a result of the increasing awareness of the severity of contracting Human Immunodeficiency Virus (HIV) and Acquired Immune Deficiency Syndrome (AIDS) through accidental needle sticks. The members of professions that must deal on a daily basis with the risk of coming in contact with people that do or may have HIV or AIDS are acutely aware of the severity. These professionals are therefore taking every precaution to reduce the risks. Members of the medical profession, especially surgeons, are in an extremely high risk position when performing operations. The knowledge that infectious diseases such as the AIDS virus can spread by an accidentally inflicted needle stick from a contaminated needle administered to the person having AIDS is the cause for much concern.

Accordingly, there has been an increasing amount of activity in the area of surgical needle tip design. In order to decrease the potential transmission of the above infectious diseases where accidental needle stick is the means for such transmission, taper point surgical needles having a blunt tip have been developed. However, these needles have no cutting edges and enlarge a hole made by the point by pure blunt dilation with no cutting action whatsoever. For example, U.S. Pat. No. 5,123,190 to McIntosh discloses a taper needle which includes a needle tip having a blunt head. The blunt tip has a part spherical or other curved shape with no sharp edge surfaces. However, as with conventional taper point needles, the blunt needle disclosed in U.S. Pat. No. 5,123,190 does not having any cutting edges.

The design techniques that can be employed to meet the above criteria are in conflict. For example, to improve needle penetration the needle point should be made as sharp as possible. But by sharpening the needle point, the penetration force needed to penetrate the gloved hand of an operator is significantly decreased. Likewise, accidental skin penetration of the gloved hand can be reduced by making a less sharper point, but this will correspondingly increase the initial force required for penetration. Thus, the design of a needle with favorable performance in both areas requires tradeoffs to be made in the two criteria to arrive at a needle with optimal overall performance. Thus, there is a need to develop an improved surgical needle which significantly reduces the probability of skin penetration of the gloved hand of an operator while being adapted to suture cutaneous tissue of the body as well as other types of tissue.

SUMMARY OF THE INVENTION

The present invention is directed to blunt tip cutting edge surgical needles which significantly reduce the probability of skin penetration of the gloved hand of an operator and are suitable for use in suturing cutaneous tissues of the body. The blunt tip surgical needles of the present invention include a cutting section and an integral blunt tip. The blunt tip blends smoothly at its circumference with the outer surface of the distal end of the cutting section such that there are no sharp edges or discontinuities at the blunt tip.

The provision of the blunt tip improves upon the prior art sharp point cutting edge needles in that the needles of the present invention are less likely to penetrate the glove and skin of the user. Although the blunt tip cutting edge needles of the present invention compromise initial forces of penetration, by retaining the sharpness of the cutting edges the net effect and benefits of the needles of the present invention are greatly increased over prior art sharp point cutting edge needles.

In one embodiment of the needle of the present invention, the needle has a tapercut configuration. More specifically, the needle has a gradually decreasing triangular cross-sectional shape throughout the cutting section and terminates in a blunt tip. The cutting section includes three cutting edges one of which is a reverse cutting edge. The blunt tip can have a triangular dome shape or a flat triangular shape with rounded corners. The blunt tip blends smoothly with the outer surface of the cutting section such that there are no sharp edges at the blunt tip. By utilizing a blunt tip, the resistance to penetration is increased over prior art sharp point tapercut needles.

In another embodiment of the present invention, the needle has a gradually decreasing concave triangular cross-sectional shape throughout the cutting section and terminates in a blunt tip. The cutting section includes three cutting edges. The blunt tip can have a triangular dome shape with each side of the triangle having a concave shape. The blunt tip can also have a flat triangular shape with concave sides and rounded corners. The blunt tip blends smoothly at its circumference with the outer surface of the distal end of the cutting section to avoid any sharp edges at the blunt tip. This blunt tip needle significantly increases the penetration force needed to penetrate a latex glove as compared to a sharp point needle having the same cross-sectional shape and cutting edges as the cutting section of the present needle.

In yet another embodiment of the present invention, the needle has a spatula configuration. More specifically, the needle has a gradually decreasing trapezoidal cross-sectional shape throughout the cutting portion and terminates in a blunt tip. The cutting portion includes four cutting edges. The blunt tip can have a trapezoidal dome shape or a flat trapezoidal shape with rounded corners both of which blend smoothly with the distal end of the cutting section to avoid sharp edges. The present needle significantly decreases the probability of skin penetration of the gloved hand of an operator as compared to a sharp point spatula needle.

In a further embodiment of the present invention, the needle has a gradually decreasing triangular cross-sectional shape from the body portion, throughout the cutting portion and ends in a blunt tip. In contrast to the tapercut embodiment described above, the base of the triangle is on the outside of the curve of the needle and the apex of the triangle is on the inside of the curve. The blunt tip has a triangular dome shape or a flat triangular shape with rounded corners. The tip of the needle makes a transition from the blunt tip to the distal end of the cutting section such that there are no sharp edges at the tip of the needle. As with the embodiments described above, the glove penetration resistance is increased as compared to prior art sharp point cutting edge needles.

BRIEF DESCRIPTION OF THE DRAWINGS

FIG. 3 is an enlarged perspective view of a portion of one embodiment of the needle of the present invention.

FIG. 4 is an enlarged front view of the tip of the surgical needle of FIG. 3.

FIG. 5 is a cross-sectional view taken along lines, 5—5 in FIG. 3.

FIG. 6 is an enlarged perspective view of a portion of another embodiment of a surgical needle according to the present invention.

FIG. 7 is an enlarged front view of the tip of the surgical needle of FIG. 6.

FIG. 8 is a cross-sectional view taken along lines 8—8 in FIG. 6.

FIG. 9 is an enlarged perspective view of a portion of another embodiment of a surgical needle according to the present invention.

FIG. 10 is an enlarged front view of the tip of the surgical needle of FIG. 9.

FIG. 11 is a cross-sectional view taken along lines 11—11 in FIG. 9.

FIG. 12 is an enlarged perspective view of a portion of yet another embodiment of a surgical needle according to the present invention.

FIG. 13 is an enlarged front view of the tip of the surgical needle of FIG. 12.

FIG. 14 is a cross-sectional view taken along lines 14—14 in FIG. 12.

DETAILED DESCRIPTION OF THE INVENTION

Figure 1:
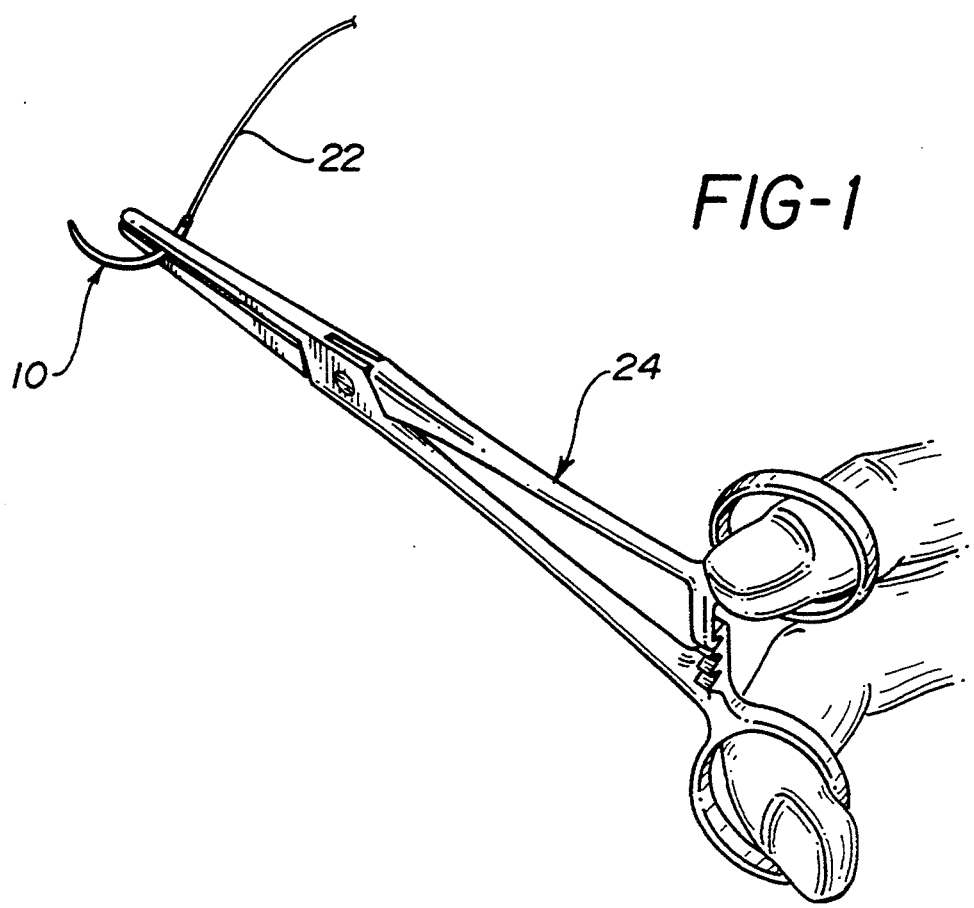
FIG. 1 is a perspective view of a sterile surgical needle in accordance with the present invention having suture swaged to one end with the needle held in a forceps-type needle holding instrument.
Figure 2:
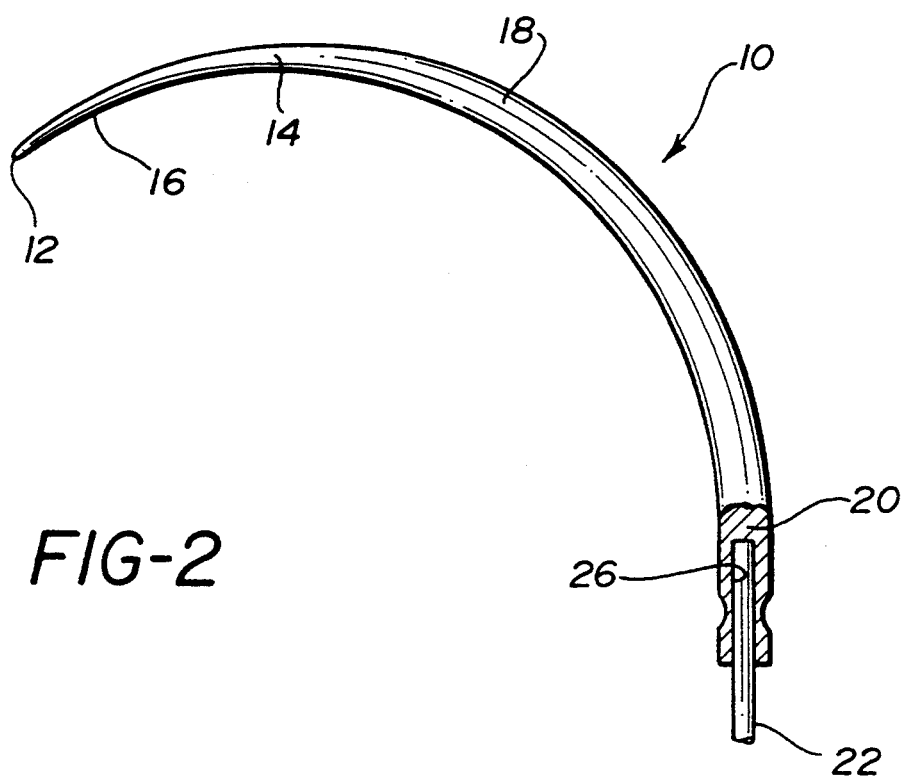
FIG. 2 is an enlarged perspective view of the surgical needle of FIG. 1.

Referring to FIG. 1, there is shown a sterile surgical needle 10 according to the present invention. As depicted in FIG. 2, the needle has a tip 12, a contiguous cutting section 14 having a cutting edge 16, a contiguous body portion 18 and a suture mounting end 20 with an appropriate suture 22 swaged into end 20. The body portion 18 can be grasped by a suitable forceps-type needle holding instrument 24. The instrument 24 places considerable force on the body of the needle. It is critical that the needle be held there so that there is no lateral movement, transverse movement or rotational movement in the needle holding instrument 24, and, hence, it is important to place sufficient force on the body of the needle so that it is adequately locked in the instrument.

As more clearly shown in FIG. 2, the suture 22 may be placed into a drilled hole 26 in the end 20 of the instrument and the needle pressed or swaged to lock the suture in place. Also, the suture mounting end 22 of needle 10 may have an appropriate channel with the suture laid in the channel and the channel crimped or swaged to lock the suture 22. Extending from the end 20 is the body portion 18 of the needle. This is the portion that is held by the instrument which is manipulated by the surgeon in placing the suture material. Extending from the body portion 18 is the cutting section 14 of the needle or very often termed the blade of the needle. The blade starts near the tip 12 of the needle and extends to the maximum width of the needle (i.e., the body portion 18). The geometric and sectional configuration of the blade will vary depending on the surgical procedure for which the suture is to be used which also determines the number of cutting edges that the blade will have.

The cross-sectional shape of the body portion 18 can have a wide variety of conventional shapes in addition to those which will be described below. For example, in any of the embodiments of the present invention the body portion 18 can have a shape selected from the group consisting of circular, square, rectangular, triangular, or flat pressed circular. In the needle 10, the body portion 18 and cutting section 14 are curved and can possess a constant radius of curvature. This configuration is, however, not critical to the present invention and body portion 18 and cutting section 14 can therefore assume any straight and/or curved configuration which is considered suitable for the particular purpose that is intended.

The needle 10 is rigidly formed of a suitable material for use in suturing cutaneous tissues, as well as other types of tissues, of the body such as surgical grade steel, martensite stainless steel, and precipitation hardened stainless steel.

Referring now to FIGS. 3, 4, and 5 there is shown a tapercut surgical needle 30 according to the present invention. The needle 30 exhibits a gradually decreasing triangular cross-sectional shape from body portion 32 throughout cutting section 34 and terminates in a blunt tip 36. The base of the triangle is on the inside of the curve and the apex of the triangle is at the outside of the curve. The cutting section 34 includes three cutting edges 38, 40, and 42 of which cutting edge 38 is a reverse cutting edge. The cutting edge 38 on the outside of the curve makes the needle 30 suitable for tough, difficult to penetrate tissues. As shown in FIG. 5, the body portion 32 exhibits a generally uniform triangular shape.

The blunt tip 36 can have a triangular dome shape as shown in FIG. 3 or a flat triangular shape with rounded corners as shown in FIG. 4. The shape of needle 30 at the tip makes a transition from the blunt tip 36 to the triangular cross-section such that there are no sharp edges or discontinuities at tip 36. The blunt tip 36 blends smoothly at its circumference with the outer surface of the distal end of cutting section 34 such that there are no sharp edges at blunt tip 36. The cutting edges 38, 40, and 42 extend from blunt tip 36 along the blade of needle 30 to body portion 32. The needle 30 of the present invention is suitable for use in suturing cutaneous tissues of the body, as well as other types of tissues, while simultaneously significantly decreasing the probability of skin penetration of the gloved hand of an operator as compared to a prior art sharp point tapercut needle.

Referring to FIGS. 6, 7, and 8, there is shown another embodiment of a surgical needle according to the present invention which is suitable for suturing cutaneous tissues of the body. The needle 50 has a gradually decreasing concave triangular cross-sectional shape that extends from the body portion 52 throughout cutting section 54 and terminates in blunt tip 56. The cutting section 54 includes three triangularly oriented concave sides 58. The needle 50 further includes three cutting edges 60 which begin near blunt tip 56 and proceed along the blade of the needle 50 towards body 52 of the needle. The body 52 of needle 50 has a flat pressed circular shape to aid in holding the needle in an appropriate needle holding instrument.

The blunt tip 56 can have a triangular dome shape with each side of the triangle being concave as shown in FIG. 6. Blunt tip 56 can also have a flat triangular shape with concave sides and rounded corners as shown in FIG. 7. The shape of needle 50 at tip 56 makes a transition from blunt tip 56 to the triangular cross-section such that there are no sharp cutting edges or discontinuities at tip 56 which makes initial contact with a surface to be penetrated. The blunt tip 56 blends smoothly at its circumference with the outer surface of the distal end of cutting section 54 such that there are no sharp edges at blunt tip 56. By utilizing blunt tip 56, the penetration force of needle 50 needed to penetrate the gloved hand of an operator is significantly increased as compared to a sharp point needle having the same cross-sectional shape and cutting edges as the cuting portion 54 of needle 50.

Turning now to FIGS. 9, 10, and 11 there is shown another embodiment of a surgical needle 62 according to the present invention. The configuration of this needle is termed a "spatula" configuration and the body 64 of the needle as more clearly shown in FIG. 11 has a trapezoidal cross-section. The cutting section 66 of needle 62 exhibits a gradually decreasing trapezoidal cross-sectional shape from body portion 64 throughout cutting portion 66 and terminates in a blunt tip 68. The cutting section 66 includes four cutting edges 70 which extend from blunt tip 68 and proceed along the blade of the needle 62 toward body 64 of the needle.

As shown in FIG. 9, the blunt tip 68 can be a trapezoidal dome shape. Blunt tip 68 can also have a flat trapezoidal shape with rounded corners as shown in FIG. 10. The tip of needle 62 makes a transition from blunt tip 68 to the trapezoidal cross-section such that there are no sharp edges or discontinuities at that part of blunt tip 68 which makes initial contact with a surface. The blunt tip 68 blends smoothly at its circumference with the outer surface of the distal end of cutting section 66 such that there are no sharp edges at tip 68. The needle 62 can be used to suture cutaneous tissues of the body while significantly decreasing the probability of skin penetration of the gloved hand of an operator as compared to a prior art needle having a "spatula" configuration and a sharp point.

Turning to FIGS. 12, 13, and 14 there is shown another embodiment of a surgical needle 72 according to the present invention which is also suitable for use in suturing cutaneous tissues. The cutting portion 74 of needle 72 exhibits a gradually decreasing triangular cross-sectional shape from body portion 76 throughout cutting portion 74 and terminates in a blunt tip 78. The base of the triangle is on the outside of the curve and the apex of the triangle is on the inside of the curve. The cutting portion 74 of needle 72 further includes three cutting edges 80 which extend from blunt tip 78 and proceed along the blade of the needle toward body 76 of the needle. The body or holding portion 76 has a flat pressed circular shape as shown in FIG. 14 to improve stability of the needle in a suitable needle holding instrument.

The blunt tip 78 can have a triangular dome shape as shown in FIG. 12. Blunt tip 78 can also have a flat triangular shape with rounded corners as shown in FIG. 13. The tip of needle 72 makes a transition from blunt tip 78 to the triangular cross-section such that there are no sharp edges or discontinuities at the part of blunt tip 78 which makes initial contact with a surface. The blunt tip 78 blends smoothly at its circumference with the outer surface of the distal end of cutting section 74 to avoid having any sharp edges at blunt tip 78. The blunt tip 78 of needle 72 significantly decreases the probability of skin penetration of the gloved hand of an operator as compared to a sharp point needle having the same cross-sectional shape and cutting edges as the cutting portion 74 of needle 72.

Most needle sticks take place at the tip of a needle while the cutting edge(s) of the needle and body geometry govern needle performance. Although the blunt tip cutting edge needles of the present invention compromise initial forces of penetration, surgeons, and other operating personnel would be able to dramatically increase their safety factor against blood transmittable diseases during surgery as a result of the blunt tip needles of the present invention. By retaining the sharpness of the cutting edges the net effect and benefits of the blunt tip cutting edge needles of the present invention are greatly increased as compared to prior art sharp point cutting edge needles. In addition, the sharpness of the cutting edges of the present needles can be increased by treating them as described in U.S. Pat. No. 4,660,559 to provide a surface hardness over the cutting edges of at least 50 measured on the Rockwell C Hardness Scale.

While the invention has been particularly shown and described with respect to illustrative and preferred embodiments thereof, it will be understood by those skilled in the art that the foregoing and other changes in form and details may be made therein without departing from the spirit and scope of the invention which should be limited only by the scope of the appended claims.

What is claimed is:

1. A surgical needle comprising:
   a body portion,
   a blunt tip, and
   a cutting portion disposed between and contiguous with said body portion and said blunt tip, said cutting portion having at least one cutting edge extending from said blunt tip to said body portion, said blunt tip blending smoothly with an outer surface of a distal end of said cutting portion such that said blunt tip has no sharp edges or discontinuities.

2. The surgical needle according to claim 1, wherein said cutting portion has a cross-sectional area which decreases progressively toward said blunt tip.

3. The surgical needle according to claim 2, wherein said cross section is triangular and said cutting portion has three cutting edges corresponding to the edges of said triangle.

4. The surgical needle according to claim 3, wherein said blunt tip has a shape selected from the group consisting of triangular dome and flat triangular with rounded corners.

5. The surgical needle according to claim 4, wherein said needle has an overall curved shape with a constant radius of curvature.

6. The surgical needle according to claim 5, wherein a base of said triangular cross-section is on an inside of said curved shape and an apex of said triangular cross-section is on an outside of said curved shape.

7. The surgical needle according to claim 5, wherein a base of said triangular cross-section is on an outside of said curved shape and an apex of said triangular cross-section is on an inside of said curved shape.

8. The surgical needle according to claim 3, wherein each side of said triangular cross-section has a concave shape.

9. The surgical needle according to claim 2, wherein said blunt tip has a shape selected from the group consisting of concave triangular dome and flat concave triangular with rounded corners.

10. The surgical needle according to claim 2, wherein said cross-section has a trapezoidal shape and said cutting portion has four cutting edges corresponding to the edges of said trapezoid.

11. The surgical needle according to claim 10, wherein said blunt tip has a shape selected from the group consisting of trapezoidal dome and flat trapezoidal with rounded corners.

12. The surgical needle according to claim 1, further including a suture mounting portion having a hole to which a suture is to be attached, said suture mounting portion being contiguous with said body portion.

13. The surgical needle according to claim 12, wherein said needle has an overall curved shape with a constant radius of curvature.

14. The surgical needle according to claim 13, wherein said body portion has a generally uniform cross-sectional area throughout an entire length thereof.

15. The surgical needle according to claim 14, wherein said cross-sectional area of said body portion has a shape selected from the group consisting of circular, square, rectangular, triangular, trapezoidal, and flat pressed circular.

* * * * *